(12) United States Patent
Paulus et al.

(10) Patent No.: US 10,639,616 B2
(45) Date of Patent: May 5, 2020

(54) EXTRUDED CU—AL—MN HYDROGENATION CATALYST

(71) Applicant: Clariant International Ltd., Muttenz (DE)

(72) Inventors: Martin Paulus, Rosenheim (DE); Frank Grossmann, München (DE); Oliver Wegner, Heufeldmühle (DE)

(73) Assignee: Clariant International Ltd, Muttenz (CH)

( * ) Notice: Subject to any disclaimer, the term of this patent is extended or adjusted under 35 U.S.C. 154(b) by 0 days.

(21) Appl. No.: 15/508,234

(22) PCT Filed: Aug. 24, 2015

(86) PCT No.: PCT/EP2015/069349
§ 371 (c)(1),
(2) Date: Mar. 2, 2017

(87) PCT Pub. No.: WO2016/037839
PCT Pub. Date: Mar. 17, 2016

(65) Prior Publication Data
US 2017/0252727 A1  Sep. 7, 2017

(30) Foreign Application Priority Data
Sep. 12, 2014  (DE) .................. 10 2014 013 530

(51) Int. Cl.
| | | |
|---|---|---|
| *B01J 23/889* | (2006.01) | |
| *B01J 35/00* | (2006.01) | |
| *B01J 37/04* | (2006.01) | |
| *B01J 35/02* | (2006.01) | |
| *B01J 35/10* | (2006.01) | |
| *B01J 37/00* | (2006.01) | |
| *B01J 37/16* | (2006.01) | |
| *C07C 29/149* | (2006.01) | |
| *B01J 37/03* | (2006.01) | |
| *B01J 37/08* | (2006.01) | |
| *C07C 31/125* | (2006.01) | |

(52) U.S. Cl.
CPC ......... *B01J 23/8892* (2013.01); *B01J 35/002* (2013.01); *B01J 35/0006* (2013.01); *B01J 35/0026* (2013.01); *B01J 35/0053* (2013.01); *B01J 35/023* (2013.01); *B01J 35/108* (2013.01); *B01J 35/1038* (2013.01); *B01J 35/1042* (2013.01); *B01J 35/1061* (2013.01); *B01J 35/1066* (2013.01); *B01J 35/1085* (2013.01); *B01J 37/0009* (2013.01); *B01J 37/031* (2013.01); *B01J 37/04* (2013.01); *B01J 37/08* (2013.01); *B01J 37/16* (2013.01); *C07C 29/149* (2013.01); *C07C 31/125* (2013.01); *B01J 37/0018* (2013.01); *B01J 37/0045* (2013.01); *B01J 37/03* (2013.01)

(58) Field of Classification Search
CPC .... B01J 23/72; B01J 23/8892; B01J 35/1038; B01J 35/1042; B01J 2523/17; B01J 2523/31; B01J 2523/72; C07C 5/02
See application file for complete search history.

(56) References Cited

U.S. PATENT DOCUMENTS

| | | |
|---|---|---|
| 3,125,571 A | 3/1964 | Chechak et al. |
| 3,287,402 A | 11/1966 | Landis |
| 3,334,149 A | 8/1967 | Akin |
| 3,555,106 A | 1/1971 | Ohmore |
| 4,012,453 A | 3/1977 | Nychka |
| 4,169,107 A | 9/1979 | Asano et al. |
| 4,176,137 A | 11/1979 | Platz et al. |
| 4,524,225 A | 6/1985 | Qualetti et al. |
| 4,666,879 A | 5/1987 | Kelly |
| 4,863,894 A | 9/1989 | Chinchen et al. |
| 4,929,777 A | 5/1990 | Irick et al. |
| 4,937,384 A | 6/1990 | Dobson |
| 5,059,273 A | 10/1991 | Boyce et al. |
| 5,124,295 A | 6/1992 | Nebesh et al. |
| 5,128,307 A | 7/1992 | Wanjek et al. |
| 5,134,108 A | 7/1992 | Thakur et al. |
| 5,155,086 A | 10/1992 | Thakur et al. |
| 5,201,552 A | 4/1993 | Hohmann et al. |
| 5,229,246 A | 7/1993 | Shibata et al. |

(Continued)

FOREIGN PATENT DOCUMENTS

| | | |
|---|---|---|
| DE | 225597 A3 | 7/1985 |
| DE | 161242 A3 | 8/1985 |

(Continued)

OTHER PUBLICATIONS

De Jong, K.P. "Synthesis of solid catalysts," Wiley-VCH Verlag, p. 175 (2009).

(Continued)

*Primary Examiner* — Jun Li

(57) ABSTRACT

The invention relates to Cu—Al—Mn shaped catalyst bodies in extruded form, and to a process for their preparation. The shaped catalyst body is suitable for the hydrogenation of organic compounds containing a carbonyl function, in particular for the hydrogenation of aldehydes, ketones and carboxylic acids and/or their esters. In particular, the shaped catalyst body is suitable for the hydrogenation of fatty acids or their esters, such as fatty acid methyl esters, to form the corresponding alcohols and dicarboxylic acid anhydrides, such as maleic anhydride, or esters of di-acids and di-alcohols, such as butane diol.

19 Claims, No Drawings

(56) References Cited

U.S. PATENT DOCUMENTS

| | | | |
|---|---|---|---|
| 5,334,779 A | 8/1994 | Kuo | |
| 5,345,005 A | 9/1994 | Thakur et al. | |
| 5,395,990 A | 3/1995 | Scarlett | |
| 5,403,962 A | 4/1995 | Schneider et al. | |
| 5,418,201 A | 5/1995 | Roberts et al. | |
| 5,550,297 A | 8/1996 | Horn et al. | |
| 5,935,898 A * | 8/1999 | Trubenbach | B01J 35/10 502/150 |
| 5,977,010 A | 11/1999 | Robert et al. | |
| 6,207,130 B1 | 3/2001 | Karveiva | |
| 6,417,135 B1 * | 7/2002 | Dyroff | B01J 23/40 502/20 |
| 6,455,464 B1 * | 9/2002 | Chen | B01D 53/86 502/344 |
| 7,759,530 B2 | 7/2010 | Houssin | |
| 7,807,603 B2 * | 10/2010 | Schlitter | B01J 23/72 502/263 |
| 8,318,120 B2 | 11/2012 | Nelson et al. | |
| 8,383,846 B2 | 2/2013 | Bazer-Bachi | |
| 8,603,938 B2 | 12/2013 | Sakamoto | |
| 8,828,903 B2 | 9/2014 | Chen | |
| 9,371,496 B2 | 6/2016 | Kester et al. | |
| 10,035,137 B2 | 7/2018 | Paulus et al. | |
| 2004/0087815 A1 * | 5/2004 | Kitamura | B01J 23/8926 568/361 |
| 2008/0280754 A1 * | 11/2008 | Toledo Antonio | B01J 23/85 502/177 |
| 2010/0022796 A1 | 1/2010 | Heidenreich et al. | |
| 2010/0121080 A1 * | 5/2010 | Chen | B01J 23/8892 549/295 |
| 2012/0271079 A1 * | 10/2012 | Xu | C07C 2/74 585/252 |
| 2015/0314273 A1 | 11/2015 | Paulus et al. | |

FOREIGN PATENT DOCUMENTS

| | | |
|---|---|---|
| DE | 242183 A1 | 1/1987 |
| DE | 3942064 A1 | 4/1991 |
| DE | 4333328 A1 | 4/1994 |
| DE | 278509 B5 | 11/1995 |
| EP | 0198243 B1 | 11/1988 |
| EP | 0384542 B1 | 8/1990 |
| EP | 0424069 B1 | 10/1990 |
| EP | 1566372 B1 | 8/2005 |
| FR | 1578433 A | 5/1972 |
| GB | 1084539 A | 9/1967 |
| GB | 1224736 A | 3/1971 |
| GB | 1402306 A | 8/1975 |
| GB | 1443393 A | 7/1976 |
| JP | S57-170861 A | 10/1982 |
| JP | H08-108072 A | 4/1996 |
| WO | 2002/040149 A2 | 5/2002 |
| WO | 2006/111997 A1 | 10/2006 |

OTHER PUBLICATIONS

Freiding, J. "Extrusion von technischen ZSM-5-Kontakten and ihre Anwendung im MTO-Prozess," Dissertation, Universitat Karlsruhe (TH) (2009), provided with English-language summary and machine translation of sections 2.5 and 5.6.

Mueller, S.P., "Einstufige Gasphasehydrierung von Dimethylmaleat zu Tetrahydrofuran an extrudierten Kupfer-Kontakten," Dissertation, Universitaet Fridericiana Karlsrueh (TH) (2005), provided with English-language summary.

* cited by examiner

EXTRUDED CU—AL—MN HYDROGENATION CATALYST

The invention relates to shaped Cu—Al—Mn catalyst bodies in extruded form, and to processes for producing them. The shaped catalyst bodies are suitable for hydrogenating organic compounds which contain a carbonyl function, more particularly for hydrogenating aldehydes, ketones, and also carboxylic acids and/or their esters. A preferred hydrogenation is that of fatty acids and/or their esters, such as fatty acid methyl esters, to the corresponding alcohols, and of dicarboxylic anhydrides, such as maleic anhydride (MAn), or esters of di-acids, to di-alcohols, such as butanediol.

BACKGROUND OF THE INVENTION

Catalysts in tablet form are generally used for hydrogenation reactions. These tablets are notable for high mechanical stability, a property determinable in the form of the side crushing strength. The stability comes about as a result of a relatively high pressure during tableting. As a result, the powder starting material is highly compressed, producing tablets having a relatively high bulk density. The high compression also reduces the pore volume and hence restricts access to the active centers. Only part of the active metal components, therefore, are available for the reaction.

Already disclosed in the prior art are catalysts in extrudate form where the powder starting material is processed by addition of a defined amount of suitable binders and by means of extrusion to give the corresponding shaped catalyst bodies. Extrudates customarily have a greater pore volume than the tablets produced from the same powder starting material.

The catalysts in extrudate form that are known in the prior art differ from the catalysts of the invention in particular in the composition, such as the metals and types of binder used, for example, and also in the physicochemical properties.

U.S. Pat. No. 5,977,010 describes a shaped catalyst body which comprises (i) at least one metal from the group consisting of copper, manganese, zinc, nickel, cobalt, and iron, and also (ii) calcium silicate and (iii) at least one clay material. These shaped catalysts are used for hydrogenating aldehydes, ketones, carboxylic acids, and carboxylic esters.

WO 92/10290 discloses shaped bodies of a copper chromite catalyst formed from a mixture of about 20 to 80 wt % of copper chromite and 20 to 80 wt % of at least one extrudable, inorganic binder material. The catalysts have a surface area of 20 to 225 m²/g, and the total pore volume is between 0.35 and 1 cm³/g. This document describes a process for producing the shaped copper chromite catalyst by extrusion of a mixture of copper chromite, an extrudable inorganic binder material, a peptizing agent, and water, and calcining of the extrudate. The shaped bodies obtained are used for hydrogenating aldehydes, ketones, carboxylic acids, and carboxylic esters.

U.S. Pat. No. 4,666,879 describes an extruded copper chromite-aluminum oxide catalyst which is produced by mixing 40 to 82 wt % of copper chromite and 18 to 60% of an extrudable aluminum oxide, typically having a pseudo-boehmite or alpha-hydroxy-boehmite structure. After being calcined, the extruded catalyst can be used for hydrogenating various carbonyl compounds in the liquid or gas phase. The catalyst has a surface area of between 20 and 225 m²/g and a bulk density of between 0.70 and 1.20 g/cm³.

WO 2006/005505 describes a process for hydrogenating organic, carbonyl-functional compounds using copper-containing catalyst tablets or catalyst extrudates having a diameter of <2.5 mm. The catalysts are produced by shaping and subsequently calcining a mixture of 50 to 80 wt % of copper oxide, 15 to 35 wt % of aluminum oxide, 2 to 20 wt % of lanthanum oxide, and copper platelets.

In the dissertation by Steffen P. Miller, University of Karlsruhe (TH), 2005, Cu/Zn catalysts in extruded form are described that are produced using boehmite-based binders.

WO 2005/058491 discloses $CuO/Al_2O_3$-containing shaped catalyst bodies in extrudate form. The catalysts are produced by mixing boehmite, which has undergone incipient etching with formic acid, with a $CuO/Al_2O_3$-containing active material and water. The mixture is then extruded to strands which are calcined at 600° C. The catalysts have a bulk density of between 790 and 960 g/l and pore volumes in the range from 0.31 to 0.59 cm³/g.

The mechanical stability of extrudates is generally lower than that of catalyst tablets, as manifested in a low side crushing strength, for example. Furthermore, the binders used in extrudates frequently have an adverse effect on catalyst performance. Major influencing parameters are the inherent activity of the binder matrix, change in the surface acidity, and diffusion effects in the matrix. These effects are described for example by K. P. de Jong in "Syntheses of solid catalysts", 2009, Wiley-VCH, p. 175, or in the dissertation by J. Freiding: "Extrusion of technical ZSM-5 catalysts and their application in the MTO process", University of Karlsruhe (TH), 2009, especially section 2.5 and section 5.6. In DE 10 2006 058800, therefore, shaped catalyst bodies which are extremely pure are explicitly claimed, in order to prevent adverse effects arising from the catalyst matrix.

It is an object of the present invention to provide shaped catalyst bodies which do not have the aforementioned drawbacks of catalyst tablets and catalyst extrudates, thus having a substantially higher pore volume and a significantly lower bulk density in conjunction with at least comparable stability and activity in comparison to conventional, tableted catalysts.

This object is achieved in accordance with the invention by using, when processing powder catalyst material into extrudates, specific binders which lead to stable shaped catalyst bodies. Through the processing of the powder catalyst material into extrudates using binders which lead to stable shaped bodies and at the same time generate a high pore volume, it has been possible to produce shaped catalyst bodies which, for comparable stability, have a substantially higher pore volume than the conventional, tableted catalysts.

SUMMARY OF THE INVENTION

The invention relates to a shaped catalyst body in extruded form, comprising Cu in an amount in the range of 20-43 wt %, preferably in the range of 25-42 wt %, Al in an amount in the range of 20-40 wt %, preferably in the range of 25-34 wt %, and Mn in an amount in the range of 1-10 wt %, preferably in the range of 2-8 wt %, more preferably in the range of 3-6 wt %, based on the total weight of the shaped catalyst body in extruded form,
wherein the shaped catalyst body has a pore volume in the range from 250 to 700 mm³/g, preferably in the range from 400 to 650 mm³/g, more preferably in the range from 450 to 600 mm³/g, determined by mercury intrusion to DIN 66133.

The invention further relates to a process for producing Cu-, Al-, and Mn-containing shaped catalyst bodies (shaped Cu—Al—Mn catalyst bodies) in extruded form, the process comprising the following steps:

(a) combining (i) at least one aqueous solution of copper compounds, aluminum compounds, manganese compounds, and optionally transition metal compounds and (ii) at least one aqueous carbonate-containing solution to form a precipitate, isolating the precipitate, optionally washing the isolated precipitate, and drying the isolated precipitate to give a dried precipitate,
(b) mixing the dry precipitate obtained in step (a) with an aluminum-containing binder selected from the group consisting of boehmite and pseudoboehmite,
(c) extruding the mixture obtained in step (b), to give an extrudate, and
(d) calcining the extrudate obtained in step (c), at a temperature in the range from 300 to 750° C., preferably in the range from 600° C. to 750° C., more particularly at about 750° C., to give an extruded shaped body.

The invention further relates to the use of Cu—Al—Mn catalysts of the invention for hydrogenating organic compounds, more particularly compounds which contain a carbonyl function.

DETAILED DESCRIPTION OF THE INVENTION

The extruded shaped catalyst bodies of the invention comprise copper in an amount in the range of 20-43 wt %, preferably in the range of 25-42 wt %, more preferably in the range of 30-35 wt %, based on the total weight of the shaped catalyst body in extruded form. The copper here is essentially in the form of copper oxide (CuO), copper-aluminum spinel (such as $CuAl_2O_4$), copper-manganese spinel (such as $CuMn_2O_4$ or $Cu_{1.5}Mn_{1.5}O_4$), elemental copper (Cu) and/or mixtures thereof.

The extruded shaped catalyst bodies of the invention comprise aluminum in an amount in the range of 20-40 wt %, preferably in the range of 25-34 wt %, based on the total weight of the shaped catalyst bodies in extruded form. The aluminum here is present essentially in the form of aluminum oxide ($Al_2O_3$), copper-aluminum spinel (such as $CuAl_2O_4$) and/or mixtures thereof.

The extruded shaped catalyst bodies of the invention comprise manganese in an amount in the range of 1-10 wt %, preferably in the range of 2-8 wt %, more preferably in the range of 3-6 wt %, based on the total weight of the shaped catalyst bodies in extruded form. The manganese here is essentially in the form of manganese oxide (MnO, $Mn_2O_3$, $Mn_3O_4$, $MnO_2$, $Mn_2O_7$), copper-manganese spinel (such as $CuMn_2O_4$ or $Cu_{1.5}Mn_{1.5}O_4$) and/or mixtures thereof.

With particular preference the extruded shaped catalyst bodies of the invention comprise copper in an amount in the range of 25-42 wt %, more particularly in the range of 30-35 wt %, aluminum in an amount in the range of 25-34 wt %, and manganese in an amount in the range of 2-8 wt %, more particularly in the range of 3-6 wt %, based on the total weight of the shaped catalyst bodies in extruded form.

The shaped catalyst body of the invention has a pore volume in the range from 250 to 700 $mm^3/g$, preferably in the range from 400 to 650 $mm^3/g$, more preferably in the range from 450 to 600 $mm^3/g$, determined by mercury intrusion to DIN 66133.

In one particularly preferred embodiment, the extruded shaped catalyst bodies of the invention comprise copper in an amount in the range of 25-42 wt %, more particularly in the range of 30-35 wt %, aluminum in an amount in the range of 25-34 wt %, and manganese in an amount in the range of 2-8 wt %, more particularly in the range of 3-6 wt %, based on the total weight of the shaped catalyst bodies in extruded form, and have a pore volume in the range from 400 to 650 $mm^3/g$, more preferably in the range from 450 to 600 $mm^3/g$, determined by mercury intrusion to DIN 66133.

The term "shaped catalyst body" in the present invention is used interchangeably with the term "catalyst", particularly when the topic is the function as such.

In one preferred embodiment the shaped catalyst body has a monomodal pore radius distribution, with 50% or more, preferably 70% or more, more preferably 80% or more of the pore volume being formed by pores having a pore radius in the range from 7 to 40 nm, the pore radius distribution and the pore volume being determined by mercury intrusion to DIN 66133.

The shaped catalyst bodies preferably have a bulk density in the range from 300 to 800 g/L, preferably in the range from 400 to 700 g/L, and more preferably in the range from 450 to 650 g/L, determined to DIN ISO 903.

In another embodiment the extruded shaped catalyst bodies of the invention comprise at least one further metal different from copper, aluminum, and manganese. This at least one further metal is preferably selected from the group consisting of alkali metal, alkaline earth metal, rare earths, Fe, Ni, Cr, Co, Zn, Zr, W, Mo, and mixtures thereof, more particularly selected from Na, Mg, Ce, Co, Zn, Zr, and mixtures thereof. The at least one further metal may be included in the form of a metal oxide of the aforementioned metals in the shaped catalyst body of the invention. The metal oxide may comprise one or more oxides of the aforementioned metals. In the shaped catalyst body the at least one further metal is present in an amount in the range of 0.1-12 wt %, preferably in the range of 1-7 wt %, more preferably in the range of 3-5 wt %, based on the total weight of the shaped catalyst bodies in extruded form. More preferably the shaped catalyst bodies comprise at least one further metal selected from the group consisting of Na, Mg, Ce, Co, Zn, Zr, and mixtures thereof in an amount in the range of 3-5 wt %, based on the total weight of the shaped catalyst bodies in extruded form.

The further metal may be present in the metal oxide in various stoichiometric compositions with the oxygen and/or in one or more different oxidation states. For example, Fe may be present as iron oxide, such as FeO, $Fe_2O_3$, $Fe_3O_4$, $Fe_2O$ or mixtures thereof, Ni as nickel oxide, such as NiO, $Ni_2O_3$, $NiO_2$, $Ni_3O_4$, or mixtures thereof, Cr as chromium oxide, such as $Cr_2O_3$, Cu chromate, such as $CuCrO_4$ or $CuCr_2O_7$, Cu chromite, such as $CuCr_2O_4$ or mixtures thereof, Co as cobalt oxide, such as CoO, $Co_2O_3$ or $Co_3O_4$, Zn as zinc oxide, such as ZnO, and Zr as zirconium oxide, such as $ZrO_2$.

In one preferred embodiment the Cu-, Al-, and Mn-containing shaped catalyst body of the invention in reduced form has a Cu metal surface, based on the amount of Cu present in the shaped catalyst bodies, in the range from 20 $m^2/g_{Cu}$ to 60 $m^2/g_{Cu}$, preferably in the range from 25 $m^2/g_{Cu}$ to 50 $m^2/g_{Cu}$, more preferably in the range from 30 $m^2/g_{Cu}$ to 45 $m^2/g_{Cu}$. The Cu metal surface of the shaped catalyst bodies is determined via the principle of $N_2O$ pulse chemisorption, as described for example in G. C. Chinchen, C. M. Hay, H. D. Vandervell, K. C. Waugh, "The measurement of copper surface areas by reactive frontal chromatography", Journal of Catalysis, volume 103, issue 1, January 1987, pages 79-86. The Cu metal surface is given by the amount of $N_2$ formed, which can be determined by way of a thermal conductivity detector.

The shaped catalyst bodies of the invention preferably possess a side crushing strength, measured according to DIN EN 1094-5, based on the length of the shaped catalyst bodies in extruded form, in the range from 5 to 40 N/mm, preferably in the range from 10 to 30 N/mm. The shaped catalyst bodies of the invention in extruded form customarily have a length in the range from 2 to 12 mm, preferably in the range from 3 to 10 mm, more particularly 4 to 7 mm. The lengths of the shaped catalyst bodies in extruded form can be determined, for example, by a commercial apparatus, such as a Retsch Camsizer®, for example. The side crushing strength and the length are typically determined for a multiplicity of shaped catalyst bodies (e.g., from 30 to 200, preferably 50 to 120, for example 100 shaped catalyst bodies). From the values obtained for the side crushing strength (in N) the arithmetic mean is formed. The side crushing strength relative to the length of the shaped catalyst bodies (in N/mm) is given by standardizing the arithmetic mean of the side crushing strength to the arithmetically averaged length of the shaped catalyst bodies in extruded form.

The extrudates preferably have a diameter in the range from 0.5 to 10 mm, more preferably in the range from 1 to 6 mm, and very preferably in the range from 1.5 to 3.5 mm. The diameter of the shaped catalyst bodies can be analyzed using a Retsch Camsizer®, for example.

In one particularly preferred embodiment the shaped catalyst bodies in extruded form have grooves in longitudinal direction having a depth in the range from 0.3 mm to 0.9 mm, preferably of about 0.7 mm, and a width in the range from 1.0 to 1.5 mm, preferably of about 1.2 mm.

The invention further relates to a process for producing Cu-, Al-, and Mn-containing shaped catalyst bodies in extruded form.

In the process of the invention for producing an extruded shaped catalyst body, first of all at least one aqueous solution of copper compounds, aluminum compounds, manganese compounds, and optionally further metal compounds, and at least one aqueous, carbonate-containing solution, are provided.

The wording "aqueous solution of copper compounds, aluminum compounds, manganese compounds, and optionally further metal compounds" in the sense of the present invention includes not only aqueous solutions but also aqueous suspensions and aqueous slurries of the copper compounds, aluminum compounds, manganese compounds, and optionally further metal compounds, preference being given to aqueous solutions. The at least one aqueous solution of copper compounds, aluminum compounds, manganese compounds, and optionally further metal compounds is prepared, for example, by dissolving, suspending and/or slurrying, preferably by dissolving, at least one copper compound, at least one aluminum compound, at least one manganese compound, and optionally one or more further metal compounds, in water, at acidic, neutral or basic pH, preferably at acidic or neutral pH.

Copper compounds, aluminum compounds, and manganese compounds that can be used are in principle all compounds of copper, aluminum, and manganese that are highly soluble in water, acids or alkalis, more particularly the salts of the stated metals, especially their nitrates, carbonates, oxides, hydroxides, hydroxocarbonates, their halides, such as chlorides, bromides, and/or iodides, and/or their sulfates. If oxides of the metals, such as copper oxide and/or aluminum oxide and/or manganese oxide, are used for preparing the aqueous solutions, then they are preferably dissolved completely or partly by addition of a suitable mineral acid. The copper in copper oxide may be present in one oxidation state or in a plurality of different oxidation states, such as copper(I) oxide, copper(II) oxide or mixtures thereof. The mineral acid is preferably selected from $HNO_3$, HCl, $H_2SO_4$, and mixtures thereof.

Preferred copper compounds are copper oxide ($Cu_2O$ and/or CuO), copper nitrate, copper chloride, copper carbonate, copper hydroxocarbonate ($CuCO_3 \cdot Cu(OH)_2$ and/or $(CuCO_3)_2 \cdot Cu(OH)_2$), copper acetate, and copper sulfate, especially copper nitrate.

Preferred aluminum compounds are aluminum nitrate, aluminum hydroxide, aluminum oxide hydrate (boehmite), aluminum chloride, alkali metal aluminates, and aluminum oxide ($Al_2O_3$), especially aluminum nitrate and Na aluminate.

Preferred manganese compounds are manganese nitrate, manganese hydroxide, manganese oxide, manganese chloride ($MnCl_2$), and manganese sulfate, manganese carbonate, more particularly manganese nitrate and manganese carbonate.

The further metal compounds are preferably selected from alkali metal compounds, alkaline earth metal compounds, rare earth metal compounds, and transition metal compounds (other than copper and manganese compounds). Particularly preferred alkali metal compounds are compounds of lithium, sodium, potassium, rubidium, and mixtures thereof, especially compounds of sodium. Particularly preferred alkaline earth metal compounds are compounds of manganese, calcium, strontium, barium, and mixtures thereof, especially compounds of calcium, barium, and mixtures thereof. Particularly preferred rare earth metal compounds are compounds of scandium, lanthanum, cerium, yttrium, neodymium, and mixtures thereof, especially compounds of cerium. Particularly preferred transition metal compounds (other than copper compounds and manganese compounds) are compounds of zinc, silicon, titanium, nickel, chromium, iron, cobalt, molybdenum, zirconium, and mixtures thereof, especially compounds of zinc, cobalt, zirconium, and mixtures thereof. The further metal compounds used are preferably compounds of the stated metals that are highly soluble in water, acids or alkalis. More particularly the salts of the metals are used. Particularly preferred are their nitrates, such as zinc, cerium and/or zirconium nitrate, their halides, such as zinc, cerium and/or zirconium chloride, bromide and/or iodide, their oxides, such as zinc, cerium and/or zirconium oxides, and/or their sulfates, such as zinc, cerium and/or zirconium sulfate. More strongly preferred are the further metal compounds selected from the group consisting of cerium nitrate, zinc chloride, zirconium chloride, and mixtures thereof. When using oxides of the stated further metals, the metals in the oxides may be present in one or in a plurality of different oxidation states. If the metals and/or their oxides, such as zinc, cerium and/or zirconium oxide, are used for preparing the aqueous solutions of further metal compounds, then they are preferably dissolved fully or partially by addition of a suitable mineral acid.

The at least one aqueous solution of copper compounds, aluminum compounds, manganese compounds, and optionally further metal compounds may be provided in the form of two or more separate aqueous solutions of copper compounds, aluminum compounds, manganese compounds, and optionally further metal compounds. For example, one or more aqueous solutions of copper compounds, one or more aqueous solutions of aluminum compounds, one or more aqueous solutions of manganese compounds, and optionally one or more aqueous solutions of further metal compounds may be provided. Alternatively to this, one or more joint aqueous solutions may also be provided. These solutions may be prepared by dissolving copper compounds and/or aluminum compounds and/or manganese compounds and/or optionally further metal compounds in a joint container. Also possible is the combining of aforementioned separate solutions to form a joint solution.

The aqueous, carbonate-containing solution is prepared preferably by dissolving at least one alkali metal carbonate (such as lithium, sodium, potassium, rubidium or cesium carbonate), alkaline earth metal carbonate (such as magnesium, calcium, strontium or barium carbonate) or ammonium carbonate, or mixtures thereof, in water. It is possible, simultaneously with or instead of the carbonates, to use the corresponding hydrogencarbonates, or any desired mixtures of carbonates and hydrogencarbonates.

Preference is given to using alkali metal carbonates, ammoniumcarbonates, alkali metal hydrogencarbonates, ammonium hydrogencarbonates or mixtures thereof, more preferably alkali metal carbonates and/or alkali metal hydrogencarbonates.

Preferred alkali metal carbonates are sodium and potassium carbonate, especially sodium carbonate. Preferred alkali metal hydrogencarbonates are sodium and potassium hydrogencarbonates, especially sodium hydrogencarbonate. Particular preference is given to using sodium carbonate and/or sodium hydrogencarbonate.

By combining the at least one aqueous solution of copper compounds, aluminum compounds, manganese compounds, and optionally further metal compounds with the at least one aqueous, carbonate-containing solution, a precipitate is formed. The precipitate is isolated, optionally washed and/or dried, and subsequently mixed with an aluminum-containing binder before being converted into an extruded shaped body.

In one embodiment, the combining in step (a) may take place by the at least one aqueous solution of copper compounds, aluminum compounds, manganese compounds, and optionally further metal compounds (either in separate solutions and/or in one or more joint solutions and/or as a solution mixture) and the at least one aqueous, carbonate-containing solution being added simultaneously into a joint container, such as a precipitation container, for example. In that case the at least two solutions are preferably introduced continuously into the reaction volume of a precipitation mixer.

In another embodiment the combining in step (a) may also take place by metering the at least one aqueous solution of copper compounds, aluminum compounds, manganese compounds, and optionally further metal compounds (either in separate solutions and/or in one or more joint solutions and/or as a solution mixture) into the at least one aqueous, carbonate-containing solution which has been placed as an initial charge (for example, in one or more containers, such as one or more precipitation containers).

In yet a further embodiment, the combining in step (a) may also take place by metering the at least one aqueous, carbonate-containing solution into the at least one aqueous solution of copper compounds, aluminum compounds, manganese compounds, and optionally further metal compounds, that solution having been placed as an initial charge (for example, in one or more containers, such as one or more precipitation containers).

Before being combined, the at least one aqueous solution of copper compounds, aluminum compounds, manganese compounds, and optionally further metal compounds is heated preferably to a temperature of more than 20° C., such as, for example, to a temperature in the range from 50° C. to 90° C., more particularly to about 80° C., during which it is preferably stirred.

Similarly, the at least one carbonate-containing solution, before being combined, is heated preferably to a temperature of more than 20° C., such as, for example, to a temperature in the range from 50° C. to 90° C., more particularly to about 80° C., and is preferably stirred at the same time.

In one preferred embodiment, both the at least one aqueous solution of copper compounds, aluminum compounds, manganese compounds, and optionally further metal compounds and the at least one carbonate-containing solution are heated to a temperature in the range from 50° C. to 90° C., more particularly to about 80° C., during which they are preferably stirred.

When the at least one aqueous solution of copper compounds, aluminum compounds, manganese compounds, and optionally further metal compounds is combined with the at least one aqueous, carbonate-containing solution, a precipitate is formed in the mixture (also referred to below as precipitate-containing solution mixture). The solutions are generally combined in a stirred container.

The container is preferably stirred with an inclined blade stirrer, propeller stirrer or other commercially customary stirrer.

In one preferred embodiment, the solutions are combined in step (a) by metering volume flows of aqueous solutions of copper compounds, aluminum compounds, manganese compounds, and optionally further metal compounds into the aqueous, carbonate-containing solution in a precipitation container. Here, the aqueous solutions of copper compounds, aluminum compounds, manganese compounds, and optionally further metal compounds may be metered as separate solutions and/or as one or more joint solutions.

The precipitate-containing solution mixture is maintained preferably at a temperature above 20° C. and more particularly at a temperature in the range from 50° C. to 90° C., preferably at about 80° C. In one particularly preferred embodiment of the invention the precipitate-containing solution mixture is maintained for at least 30 minutes, preferably 1 to 36 hours, more particularly about 2 hours, at a temperature in the range from 50° C. to 90° C., preferably at a temperature of about 80° C., in order, where appropriate, to complete the formation of the precipitate and/or to increase the crystallinity of the precipitate by aging.

During the entire time, the pH of the mixture is maintained preferably at a level in the range from 5.0 to 8.5, more particularly in the range from 6.0 to 7.5, preferably at about 6.8.

The precipitate is isolated preferably by filtration. Alternatively to this, the precipitate may also be isolated by decanting or centrifuging. The isolated precipitate is subsequently subjected to drying. Drying may take place by means of spray drying, for example. For this purpose, a suspension having a solids content of 10 to 40 wt % is prepared from the isolated precipitate, such as a filter cake, with water. This suspension is preferably metered subsequently via a nozzle into a spray drier. The temperature in the spray drier during drying is preferably in a range from 75° C. to 130° C., more particularly in a range from 90° C. to 120° C. The exit temperature characteristic of the drying is preferably in the range from 90° C. to 120° C. and is customarily controlled by the parameters, such as amount of suspension sprayed in, solids content of the suspension (and hence the amount of water requiring evaporation), and/or temperature in the spray drier. The treatment of the material with the spray drier results in particular in a dry powder.

The isolated precipitate prior to drying may optionally be subjected to one or more washing steps. In that case the precipitate may first be isolated from the precipitate-containing solution mixture by using a filter press, then subjected to a flow of water in the filter press, which washes the precipitate. Alternatively, following isolation from the precipitate-containing solution mixture, the isolated precipitate may be slurried by filtration, decanting or centrifuging in a container, and then again separated from the liquid phase with the aid of a filter press, a centrifuge or a decanter. This operation is generally carried out one or more times until the filtrate attains a defined conductivity. The conductivity here generally correlates with the concentration of sodium ions.

The conductivity of the filtrate from the last washing procedure is preferably 0.5 mS/cm or less, more particularly 0.2 mS/cm or less. The conductivity is determined to DIN 38404, Part 8.

The dried precipitate obtained in step (a) described above is subsequently mixed, in a step (b), with an aluminum-containing binder.

In a further embodiment, step (b) encompasses steps (b1), (b2), and (b3). A part of the dried precipitate obtained in step (a) is in this case subjected to calcining in a step (b1). This calcined precipitate obtained in step (b1) is then mixed, in a step (b2), with a further part of the dried (uncalcined) precipitate obtained in step (a), and the resulting mixture is thereafter mixed, in a step (b3), with an aluminum-containing binder.

The calcining in step (b1) is done by thermal treatment, the temperature being in the range from 250° C. to 900° C., preferably in a range from 300° C. to 750° C., more preferably in a range from 600° C. to 750° C. Calcining can be performed under air, inert gas (such as argon or nitrogen, for example), oxygen or mixtures thereof. Calcining may be performed discontinuously, in a tray furnace, for example, or continuously, in a rotary tube furnace, for example. Calcining in the rotary tube furnace can be controlled through the residence time and different heating zones. The rotary tube furnace preferably has 1 to 10 different heating zones, more particularly around five heating zones. The temperature in the different heating zones is situated, for example, in the range from 300° C. to 400° C. for the first heating zone, in the range from 500° C. to 600° C. for the second heating zone, in the range from 600 to 750° C. for the third heating zone, in the range from 650° C. to 800° C. for the fourth heating zone, and in the range from 500° C. to 700° C. for the fifth heating zone. The residence time in the different heating zones is preferably in the range from 5 min to 60 min, more particularly in the range from 10 min to 30 min. When a tray furnace is used, the dried precipitate obtained in step (a) is usually spread onto metal sheets. In the tray furnace, temperature profiles can be controlled by appropriate furnace control. The temperature profile may, for example, encompass heating at a heating rate of 2° C./min from 20° C. to 750° C., holding at 750° C. for 3 h, and cooling at a cooling rate of 2° C./min to 20° C.

In step (b2), the calcined precipitate obtained by the calcining in step (b1) is mixed with dried uncalcined precipitate obtained in step (a), in a weight ratio of uncalcined precipitate to calcined precipitate in the range from 2:98 to 98:2, preferably in the range from 10:90 to 90:10, more preferably in the range from 15:85 to 85:15, and very preferably in the range from 20:80 to 50:50. The resulting mixture of uncalcined and calcined precipitate is thereafter mixed with an aluminum-containing binder in a step (b3).

For the catalyst of the invention, preference is given to using an aluminum oxide-based, aluminum-containing binder. The aluminum oxide-based, aluminum-containing binder is in that case selected with particular preference from the group consisting of boehmite (AlO(OH)) and pseudoboehmite (gelatinous/colloidal boehmite). Boehmite is described in particular in the 9th edition of Strunz'schen Mineralsystematik; E. Schweizerbat'sche Verlagsbuchhandlung (Nägele u. Obermiller), Stuttgart 2001: Group 4.FE.15.

The aluminum oxide-based, aluminum-containing binder which is mixed in step (b) or (b3) with the dry precipitate obtained in step (a) or with the mixture obtained in step (b2), respectively, is peptized with an acid, this peptizing taking place prior to mixing and/or during mixing. The peptizing procedure is a key step in the generation of the pore volume. Peptizing can be carried out using not only inorganic acids such as $HNO_3$, $H_2SO_4$ or HCl but also organic acids. Using strong inorganic acids or strong organic acids, such as formic acid, leads in general to a lower pore volume. For peptizing in accordance with the present invention, preference is given to using organic acids other than formic acid, preferably acetic acid or citric acid. The acid is used in an amount in the range of 0.5 and 0.01 wt %, based on the amount of aluminum-containing binder. In the case of dilute acids, such as 50% strength acetic acid, for example, the amount of undiluted acid is taken as the basis for calculating the acid amount/binder ratio.

The boehmite and/or pseudoboehmite used is employed preferably in the form of powder. The powder preferably has a particle size $D_{50}$ in the range from 10 to 40 µm, preferably from 15 to 35 µm, and more preferably from 20 to 30 µm, determined by the laser diffraction method to DIN ISO 13320. The boehmite or pseudoboehmite used preferably has a pore volume in the range of 300-700 mm$^3$/g, preferably in the range of 400-600 mm$^3$/g, and more preferably in the range of 450-550 mm$^3$/g. In one preferred embodiment, boehmite and/or pseudoboehmite is used in powder form with a particle size $D_{50}$ in the range from 10 to 40 µm and a pore volume in the range of 300-700 mm$^3$/g, more preferably with a particle size $D_{50}$ in the range from 15 to 35 µm and a pore volume in the range of 400-600 mm$^3$/g, more particularly with a particle size $D_{50}$ in the range from 20 to 30 µm and a pore volume in the range of 450-550 mm$^3$/g.

Suitable boehmite or pseudoboehmite powders are sold for example by Sasol under the name Pural or by Akzo Nobel or Nabaltec.

Mixing of the dried precipitate obtained in step (a) or of the mixture of calcined and uncalcined precipitate obtained in step (b2) with the aluminum-containing binder described above can be accomplished by methods known to the skilled person that ensure mixing. For example, mixing may take place in intensive mixers such as an Eirich mixer or else by means of plowshare mixers or Lödiger mixers. Kneading devices as well can be used for the mixing of powders.

The mixture obtained in step (b) or in step (b3) is subsequently extruded in step (c) by methods known to the skilled person to form shaped catalyst bodies, to give an extrudate. Examples of extrudates are rods and ribbed rods.

Prior to extrusion, the mixture obtained in step (b) or in step (b3) is preferably admixed with a lubricant in an amount in the range from 0.1 to 5 wt %, based on the total weight of the material to be extruded. More preferably the lubricant is added in an amount in the range from 0.5 to 5 wt %, even more preferably in the range from 1 to 4 wt %, based on the total weight of the material to be extruded. The lubricant is preferably graphite, oil or fatty acid salt, preferably graphite or steatite oil.

The extrudate obtained in step (c) is optionally dried in step (c1). The extrudate can be dried by heating to a temperature in the range from 75° C. to 130° C., in a furnace, for example, such as a tray furnace.

Thereafter the extrudate obtained in step (c) or the dried extrudate obtained in step (c1) is calcined in step (d) at a temperature in the range from 300° C. to 750° C., preferably in the range from 600° C. to 750° C., more particularly at about 750° C., to give an extruded shaped body.

In a further embodiment, the extruded shaped catalyst body obtained in step (d) is reduced in a step (e).

Reducing takes place preferably by heating of the extruded shaped catalyst body in a reducing atmosphere. The reducing atmosphere more particularly is hydrogen. Reducing takes place for example at a temperature in the range from 150° C. to 450° C., more particularly in the range from 180° C. to 250° C., preferably in the range from 190° C. to 210° C., more preferably at about 200° C. Reducing takes place for example over a period of 1 hour to 10 days, more particularly over a period of 2 hours to 72 hours, preferably over a period of 24 to 48 hours. In one preferred embodiment the reducing takes place at a temperature in the range from 190° C. to 210° C. over a period of 24 to 48 hours.

Following reduction, the shaped catalyst bodies are preferably stabilized wet or dry. In the case of wet stabilization, the shaped bodies are covered with liquid in order to prevent as far as possible contact with oxygen. Suitable liquids include organic liquids and water, preferably organic liquids. Preferred organic liquids are those having a vapor pressure at 20° C. at 0.5 hPa or less. Examples of suitable organic liquids are isodecanol, Nafol, fatty alcohols, hexadecane, 2-ethylhexanol, propylene glycol, and mixtures thereof, especially isodecanol.

In the case of dry stabilization, a mixture of oxygen or an oxygen-containing gas, preferably air, and an inert gas, such as argon or nitrogen, is metered into the reduction reactor. The concentration of oxygen in the mixture is raised preferably from about 0.04 vol % to about 21 vol %. For example, a mixture of air and inert gas can be metered in, with the ratio of air to inert gas at the start being about 0.2 vol % air to 99.8 vol % inert gas. The ratio of air to inert gas is then gradually increased (e.g., continuously or in steps) until, ultimately, for example, 100 vol % air is metered in (corresponding to an oxygen concentration of around 21 vol %). Without being tied to any theory, it is supposed that the metered addition of air or oxygen forms a thin oxide layer having a thickness of, for example, 0.5 to 50 nm, preferably 1 to 20 nm, more particularly 1 to 10 nm, on the surface of the catalyst, thereby protecting the shaped catalyst body from further oxidation. In the case of the dry stabilization, the reactor temperature is preferably 100° C. or less, more preferably 20° C. to 70° C., and very preferably 30° C. to 50° C. After this stabilization, the shaped catalyst body is "transportable" and can be transported to the user/plant operator. Where the catalyst user performs step (e) in situ in the reactor, stabilization is customarily omitted.

The shaped catalyst bodies of the invention are suitable for use in numerous reactions. Possible reactions include synthesis gas reactions, methanol syntheses, Fischer-Tropsch synthesis, pyridine syntheses, ester hydrogenolyses, amination reactions, N-alkylations, hydrogenations of nitriles to amines, hydrogenation of acrylonitrile, hydrogenation of fatty acid esters, hydrogenation of diesters to diols (especially maleic esters), hydrogenation of sugars to polyols, alkylation of a phenol with alcohol, amination of an alcohol, dehydrogenation of an alcohol, hydrogenation of an aldehyde, hydrogenation of an amide, hydrogenation of a fatty acid, by esterification and subsequent hydrogenolysis, for example; selective hydrogenation of a fat, selective hydrogenation of an oil, hydrogenation of a nitrile, hydrogenation of a nitroaromatic hydrocarbon, hydrogenation of a ketone, hydrogenation of furfural, hydrogenation of an ester, and hydrogenation of carbon monoxide to methanol.

In a preferred embodiment, the catalysts produced by the process of the invention are used in the hydrogenation of carbonyl compounds, more particularly for the hydrogenation of aldehydes, ketones, carboxylic acids and/or their esters or dicarboxylic acids and/or their diesters, very preferably for the hydrogenation of fatty acid esters, more particularly fatty acid alkyl esters, preferably fatty acid methyl esters, or maleic esters.

The shaped catalyst body of the invention is especially suitable for the liquid-phase hydrogenation of carboxylic acids, preferably of fatty acids and/or fatty acid mixtures having 5 to 24 C atoms and/or esters thereof, optionally in a mixture with alcohols, to give the corresponding fatty alcohols. In this case the fatty acids or fatty acid mixtures may be esterified in situ with alcohols present in the reaction mixture. Preferred alcohols present in the reaction mixture are fatty alcohols or mixtures of fatty alcohols having 5 to 24 C atoms. Particularly preferred is the use of the above-described catalyst for the hydrogenation of fatty acid methyl ester.

Determination of Physical Parameters

The physical parameters described in the present specification are determined as follows unless otherwise stated:

Conductivity is determined to DIN 38404, Part 8.

Particle size $D_{50}$ is determined by the laser diffraction method to DIN ISO 13320.

Residual loss on ignition is determined to DIN EN 196-2.

Pore volume and pore radius distribution are determined by mercury intrusion to DIN 66133.

Cu metal surface area is determined using $N_2O$ pulse chemisorption.

Side crushing strength is determined in accordance with DIN EN 1094-5. The side crushing strength is obtained customarily from the arithmetic mean of 100 measurements.

The length distribution of the shaped catalyst bodies is determined using a Camsizer® from Retsch GmbH, Germany.

The length reported for the shaped catalyst bodies is customarily the arithmetic mean of the lengths measured.

EXAMPLES

The invention is elucidated in more detail by means of the following, nonlimiting examples. Although these examples describe specific embodiments of the invention, they serve only to illustrate the invention and are not to be interpreted as restricting the invention in any way whatsoever. As the skilled person is aware, numerous modifications may be made to the embodiments without deviating from the scope of protection of the invention as it is defined by the appended claims.

Reference Example 1 (Production of the Uncalcined Material)

The uncalcined material is produced via precipitation of the metal nitrates with sodium carbonate to give their carbonates, after which the precipitate is filtered off, washed, and spray-dried.

Solution 1 is prepared from 1250 g of $Cu(NO_3)_2 \times 3\ H_2O$, 220 g of $Mn(NO_3)_2 \times 4\ H_2O$, 1800 g of $Al\ (NO_3)_3 \times 9\ H_2O$, and 9 L of $H_2O$. Solution 2 is prepared from 1720 g of $Na_2CO_3$ and 7.5 L of $H_2O$. The two solutions are heated to 80° C., being stirred in the process. They are then metered into a precipitation container. The pH in the precipitation container is 6.8. The volume flow rates of solutions 1 and 2 are set such that this pH is established. As soon as the two solutions have been consumed, the precipitate formed is filtered off and washed with water. The filter cake is then resuspended in about 2 L of water and spray-dried. The resulting dried but as yet uncalcined material in powder form is the starting material for the further preparations.

Reference Example 2 (Production of the Calcined Material)

Calcined material is produced by calcining uncalcined material (produced as described in reference example 1) in a forced air oven at 730° C. for 3 hours. The residual loss on ignition at 1000° C. (LOI) is about 5%.

Example 1 (Production of Shaped Catalyst Body 1)

For producing catalyst 1, 17 g of Pural SCF 55 are peptized with 34 g of 2.5% strength acetic acid and then mixed with 320 g of uncalcined material (produced as described in reference example 1) and 165 g of deionized water in a double-Z kneader. The mixture is admixed with 10 g of steatite oil as lubricant. Thereafter the mixture is extruded to rods having a diameter of 3.2 mm and a length in the range from 3 to 10 mm. The extrudates are dried at 120° C. for 16 hours and then calcined at 750° C. for 3 hours.

Example 2 (Production of Shaped Catalyst Body 2)

For producing catalyst 2, 125 g of Pural SCF 55 are peptized with 250 g of 2.5% strength acetic acid and then mixed with 720 g of uncalcined material (produced as described in reference example 1) and 370 g of deionized water in a double-Z kneader. The mixture is admixed with 20 g of steatite oil as lubricant. Thereafter the mixture is extruded to rods having a diameter of 3.2 mm and a length in the range from 3 to 10 mm. The extrudates are dried at 120° C. for 16 hours and then calcined at 750° C. for 3 hours.

Example 3 (Production of Shaped Catalyst Body 3)

For producing catalyst 3, 600 g of Pural SCF 55 are peptized with 1200 g of 2.5% strength acetic acid and then mixed with 1950 g of uncalcined material (produced as described in reference example 1) and 1000 g of deionized water in a double-Z kneader. The mixture is admixed with 80 g of steatite oil as lubricant. Thereafter the mixture is extruded to rods having a diameter of 3.2 mm and a length in the range from 3 to 10 mm. The extrudates are dried at 120° C. for 16 hours and then calcined at 750° C. for 3 hours.

Example 4 (Production of Shaped Catalyst Body 4)

For producing catalyst 4, 173 g of Pural SCF 55 are peptized with 346 g of 2.5% strength acetic acid and then mixed with 320 g of uncalcined material (produced as described in reference example 1) and 165 g of deionized water in a double-Z kneader. The mixture is admixed with 15 g of steatite oil as lubricant. Thereafter the mixture is extruded to rods having a diameter of 3.2 mm and a length in the range from 3 to 10 mm. The extrudates are dried at 120° C. for 16 hours and then calcined at 750° C. for 3 hours.

Example 5 (Production of Shaped Catalyst Body 5)

For producing catalyst 5, 262 g of Pural SCF 55 are peptized with 520 g of 2.5% strength acetic acid and then mixed with 320 g of uncalcined material (produced as described in reference example 1) and 165 g of deionized water in a double-Z kneader. The mixture is admixed with 17.5 g of steatite oil as lubricant. Thereafter the mixture is extruded to rods having a diameter of 3.2 mm and a length in the range from 3 to 10 mm. The extrudates are dried at 120° C. for 16 hours and then calcined at 750° C. for 3 hours.

Example 6 (Production of Shaped Catalyst Body 6)

Shaped catalyst body 6 is produced as for shaped catalyst body 3 (as described in example 3), with the difference that a die for grooved extrudates is used for the extrusion (diameter approximately 3.2 mm). Drying and calcining took place likewise in analogy to the procedures described in example 3. The finished extrudates have three grooves in the longitudinal direction, with a depth of about 0.7 mm and a width of about 1.2 mm.

Example 7 (Production of Shaped Catalyst Body 7)

For the production of catalyst 7, 600 g of Pural SCF 55 are mixed with 1950 g of uncalcined material (produced as described in reference example 1) in a double-Z kneader. Then first 1200 g of 2.5% strength acetic acid and, immediately thereafter, 1000 g of deionized water are added and the resulting mixture is kneaded for 60 minutes. After kneading has been carried out, 80 g of steatite oil as lubricant are admixed to the mixture and the mixture is subsequently extruded (diameter 3.2 mm). The extrudates are dried at 120° C. for 16 hours and then calcined at 750° C. for 3 hours.

Comparative Example 1 (Production of Reference Catalyst A)

For the production of reference catalyst A, 100 g of calcined material (produced as described in reference example 2) and 3 g of graphite are mixed and tabletted to form shaped bodies having a diameter of around 3 mm and a height of around 3 mm.

Comparative Example 2 (Production of Reference Catalyst B)

For the production of reference catalyst B, 150 g of Volclay SPV are mixed with 450 g of uncalcined material (produced as described in reference example 1) and 50 g of deionized water. The mixture is subsequently extruded (diameter 3.2 mm). The extrudates are dried at 120° C. for 16 hours and then calcined at 750° C. for 3 hours.

Comparative Example 3 (Production of Reference Catalyst C)

For the production of reference catalyst C, 375 g of Ludox AS40 are mixed with 450 g of uncalcined material (produced as described in reference example 1), 10 g of Zusoplast C-92 (compression and lubricity aid), and 250 g of deionized water. The mixture is subsequently extruded (diameter 3.2 mm). The extrudates are dried at 120° C. for 16 hours and then calcined at 750° C. for 3 hours.

Determination of Pore Volume

The pore volume is determined by mercury intrusion to DIN 66133. Table 1 shows the pore volume of the inventive catalysts and reference catalysts:

TABLE 1 pore volume of the inventive shaped catalyst bodies and reference catalysts

| | Pore Volume [mm³/g] | Relative pore volume [mm³/g] Pore radius ranges | | | |
|---|---|---|---|---|---|
| | | 7500-875 nm | 875-40 nm | 40-7 nm | 7-3.7 nm |
| Cat. 1 | 290 | 5.8 | 7.2 | 267.1 | 9.9 |
| Cat. 2 | 463 | 1.9 | 13 | 432.9 | 15.3 |
| Cat. 3 | 497 | 2.5 | 10.4 | 463.7 | 20.4 |
| Cat. 4 | 520 | 5.2 | 12.5 | 476.1 | 26.2 |
| Cat. 5 | 550 | 2.9 | 11.1 | 508.9 | 27.1 |
| Cat. 6 | 515 | 5.5 | 12.4 | 471.8 | 25.3 |
| Cat. 7 | 451 | 0.4 | 23.1 | 393.2 | 34.5 |
| Ref. cat. A | 150 | 0 | 0 | 136.9 | 13.1 |
| Ref. cat. B | 336 | 0 | 0 | 118 | 218 |
| Ref. cat. B | 463 | 2.7 | 45.3 | 379 | 35.7 |

Chemical Analysis

For chemical analysis of the catalysts, they are first brought into solution with a fused potassium disulfate melt, and then the chemical composition is determined by the method of ICP (inductively coupled plasma). Table 2 shows the chemical compositions of the various catalysts.

The values are reported without loss of ignition. The loss of ignition was determined according to DIN ISO 803/806.

TABLE 2 chemical composition of the various catalysts

| | Cu [wt %] | Mn [wt %] | Al [wt %] | Si [wt %] | LOI (1000° C.) [wt %] |
|---|---|---|---|---|---|
| Cat. 1 | 41.9 | 6.6 | 20.4 | — | 3.6 |
| Cat. 2 | 37.5 | 5.9 | 24.6 | — | 3.6 |
| Cat. 3 | 34.3 | 5.4 | 27.3 | — | 3.7 |
| Cat. 4 | 28.7 | 4.5 | 33.1 | — | 3.7 |
| Cat. 5 | 24.3 | 3.8 | 37.3 | — | 3.6 |
| Cat. 6 | 34.8 | 5.3 | 27.1 | — | 3.5 |
| Cat. 7 | 34.2 | 5.5 | 27.5 | — | 3.8 |
| Ref. cat. A | 45.0 | 6.5 | 18.0 | — | 7.0 |
| Ref. cat. B | 32.4 | 4.9 | 15.9 | 8.6 | 1.9 |
| Ref. cat. B | 31.0 | 4.7 | 12.4 | 15.3 | 5.0 |

Determination of Particle Size Distribution (Binder Materials)

The particle sizes are determined by the laser diffraction method to DIN ISO 13320 using a Malvern Mastersizer 2000 in accordance with the manufacturer's instructions, the sample being homogenized in deionized water prior to measurement, without any auxiliaries added, and treated with ultrasound for 5 minutes. The D values reported are based on the sample volume.

Determination of Cu Metal Surface Area

The Cu metal surface area of the catalysts is determined via the principle of $N_2O$ decomposition ($N_2O$ pulse chemisorption):

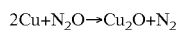

$$2Cu + N_2O \rightarrow Cu_2O + N_2$$

This is done by reducing the sample with hydrogen in a TRACE GC ULTRA reduction furnace (from Brechbühler) at 240° C. for 16 hours (forming gas 5% $H_2$ in He). The sample is then transferred to the TPDRO 1100 Series instrument from Thermo Electron and flushed with He, and the $N_2O$ pulse chemisorption is commenced. The CU metal surface area is given by the amount of $N_2$ formed in He, which is determined via a thermal conductivity detector.

TABLE 3

Cu metal surface areas of the inventive catalysts and reference catalysts

| | Cu metal surface area per g of sample [m²/g$_{sample}$] | Cu metal surface area per g of Cu [m²/g$_{Cu}$] |
|---|---|---|
| Cat. 1 | 9.1 | 21.7 |
| Cat. 2 | 11.3 | 30.1 |
| Cat. 3 | 12.6 | 36.7 |
| Cat. 4 | 15.0 | 52.3 |
| Cat. 5 | 20.0 | 82.4 |
| Cat. 6 | 12.5 | 36.4 |
| Cat. 7 | 13.2 | 38.6 |
| Ref. cat. A | 6.7 | 14.9 |
| Ref. cat. B | 8.3 | 25.6 |
| Ref. cat. B | 7.5 | 24.2 |

Determination of Bulk Density

The bulk density is determined to DIN ISO 903. Table 4 shows the bulk density of the various catalysts.

TABLE 4 bulk densities of the inventive catalysts and reference catalysts

| | Bulk density [g/L] |
|---|---|
| Cat. 1 | 680 |
| Cat. 2 | 585 |
| Cat. 3 | 550 |
| Cat. 4 | 530 |
| Cat. 5 | 490 |
| Cat. 6 | 530 |
| Cat. 7 | 550 |
| Ref. cat. A | 1500 |
| Ref. cat. B | 600 |
| Ref. cat. B | 550 |

Determination of Side Crushing Strength

The side crushing strength is determined to DIN EN 1094-5. The side crushing strength is given by the arithmetic mean of 100 measurements. For the extrudates, the side crushing strength is reported based on the length of the measured extrudates in N per mm extrudate length, the length of the extrudates being the arithmetic mean of the measured lengths of around 100 shaped catalyst bodies in extruded form. In relation to the tablets, a specific value for the side crushing strength can be reported, by virtue of the consistent dimensions.

TABLE 5 side crushing strengths of the inventive catalysts and reference catalysts

| | Side crushing strength |
|---|---|
| Cat. 1 | 4.5 N/mm |
| Cat. 2 | 11.6 N/mm |
| Cat. 3 | 13.8 N/mm |
| Cat. 4 | 15.1 N/mm |
| Cat. 5 | 18.2 N/mm |
| Cat. 6 | 10.5 N/mm |
| Cat. 7 | 15.3 N/mm |
| Ref. cat. A | 85.0 N |
| Ref. cat. B | 56 N/mm |
| Ref. cat. C | 22 N/mm |

Example 8 (Activity Measurements)

The activity of the catalysts is investigated in relation to the hydrogenation of fatty acid methyl ester (FAME). This is done using an electrically heated fixed-bed reactor having a reactor volume of 25 ml. The test is carried out using lauric acid methyl ester (C12 methyl ester). For evaluation of the ester conversion and of the selectivity with respect to the fatty alcohol and with respect to the formation of byproducts, respectively, the reaction product formed is analyzed by gas chromatography. The conversion is calculated from the amount-of-substance of ester used and from the remaining amount-of-substance of ester in the product.

For the analysis by gas chromatography, 6.0000 g of the product formed are mixed with 0.2000 g of 5-nonanol (internal standard). The sample is subsequently analyzed twice using a gas chromatograph.

Equipment Used:
GC: Agilent 7890A with FID
Column: ZB-1, 60 m×0.25 mm from Phenomenex
Software: EZ Chrom Elite Version 3.3.2 SP1
Test conditions in the hydrogenation of lauric acid methyl ester:
Reaction temperature: 160° C., 180° C., 240° C.
Pressure: 280 bar
GHSV ($H_2$): 20 000 $h^{-1}$
LHSV (ester): 1.4 $h^{-1}$ In table 1, the results for the catalysts described are reported as values for the conversions of C12 methyl ester at 180° C. Clearly apparent are the improved activity and selectivity of the inventive catalysts in comparison to the comparative catalysts.

TABLE 6 conversions of C12 methyl ester and formation of paraffin byproducts at 160° C., 180° C., and 240° C.

| | Conversion of C12 methyl ester [%] | | | Selectivity with respect to paraffin [%] | | |
|---|---|---|---|---|---|---|
| | 240° C. | 180° C. | 160° C. | 240° C. | 180° C. | 160° C. |
| Shaped catalyst body 1 | 92.0 | 70.1 | 60.0 | 1.2 | 0.2 | 0.0 |
| Shaped catalyst body 2 | 98.3 | 80.3 | 61.5 | 1.1 | 0.0 | 0.0 |
| Shaped catalyst body 3 | 98.9 | 84.3 | 61.0 | 1.2 | 0.1 | 0.0 |
| Shaped catalyst body 4 | 98.0 | 83.8 | 61.0 | 1.2 | 0.1 | 0.0 |
| Shaped catalyst body 5 | 95.0 | 75.1 | 61.0 | 1.1 | 0.1 | 0.0 |
| Shaped catalyst body 6 | 99.1 | 86.0 | 63.4 | 0.8 | 0.0 | 0.0 |
| Shaped catalyst body 7 | 98.9 | 84.7 | 61.2 | 1.1 | 0.0 | 0.0 |
| Reference catalyst A | 97.8 | 81.3 | 60.5 | 1.5 | 0.2 | 0.1 |
| Reference catalyst B | 51.2 | 23.2 | 12.3 | 1.8 | 0.3 | 0.3 |
| Reference catalyst C | 78.9 | 65.0 | 39.8 | 1.5 | 0.2 | 0.3 |

In table 6 it is evident that the shaped catalyst bodies produced in accordance with the invention are distinguished by a significantly increased conversion of lauric acid methyl ester and an increased selectivity, i.e., reduced formation of the paraffin byproduct, in comparison to the comparative catalysts. This increase was observed at all three temperatures selected, 160° C., 180° C., and 240° C.

In summary, therefore, it can be stated that by means of the shaped catalyst body of the invention, an improvement in productivity is achieved, more particularly an increase in the conversion to the target product.

The invention claimed is:

1. A shaped catalyst body, comprising Cu in an amount in the range of 20-43 wt %, Al in an amount in the range of 20-40 wt %, and Mn in an amount in the range of 1-10 wt %, based on the total weight of the shaped catalyst body, wherein the shaped catalyst body has a pore volume in the range from 250 to 700 $mm^3/g$, determined by mercury intrusion to DIN 66133, and wherein the shaped catalyst body has a monomodal pore radius distribution and wherein 50% or more of the pore volume is formed by pores having a pore radius in the range from 7 to 40 nm, the pore radius distribution and the pore volume being determined by mercury intrusion to DIN 66133, and wherein the shaped catalyst body in reduced form has a Cu metal surface, based on the amount of Cu in the shaped catalyst body, in the range from 20 $m^2/g_{Cu}$ to 60 $m^2/g_{Cu}$, determined by $N_2O$ pulse chemisorption, and wherein the shaped catalyst body has a bulk density in the range from 300 to 800 g/L, determined to DIN ISO 903, and wherein the shaped catalyst body is in the form of an calcined extrudate and has a side crushing strength, based on the length of the extrudates, in the range from 5 to 40 N/mm, the side crushing strength being determined to DIN EN 1094-5, the shaped catalyst body being made by a process comprising
(a) providing a copper, manganese and aluminum-containing dried precipitate,
(b) forming a mixture of the dry precipitate of (a) with an aluminum-containing binder selected from the group consisting of boehmite and pseudoboehmite, the aluminum-containing binder being peptized by treatment with acid,
(c) extruding the mixture obtained in (b), to provide an extrudate, and
(d) calcining the extrudate obtained in (c), at a temperature in the range from 300 to 750° C. to give a calcined extrudate.

2. The shaped catalyst body as claimed in claim 1, wherein the shaped catalyst body has a monomodal pore radius distribution and wherein 80% or more of the pore volume is formed by pores having a pore radius in the range from 7 to 40 nm, the pore radius distribution and the pore volume being determined by mercury intrusion to DIN 66133.

3. The shaped catalyst body as claimed in claim 1, having a bulk density in the range from 400 to 700 g/L, determined to DIN ISO 903.

4. The shaped catalyst body as claimed in claim 1, comprising at least one further metal selected from the group consisting of alkali metal, alkaline earth metal, rare earths, Fe, Ni, Cr, Co, Zn, and Zr.

5. The shaped catalyst body as claimed in claim 1, wherein the shaped body has a side crushing strength, based on the length of the extrudates, in the range from 10 to 30 N/mm, the side crushing strength being determined to DIN EN 1094-5.

6. The shaped catalyst body as claimed in claim 1, wherein the shaped body has a diameter in the range from 1 to 6 mm.

7. The shaped catalyst body as claimed in claim 1, wherein the shaped body has grooves in longitudinal direction having a depth in the range from 0.3 mm to 0.9 mm, and a width in the range from 1.0 to 1.5 mm.

8. The shaped catalyst body as claimed in claim 1, wherein the shaped catalyst body in reduced form has a Cu metal surface, based on the amount of Cu in the shaped catalyst body, in the range from 25 $m^2/g_{Cu}$ to 50 $m^2/g_{Cu}$, determined by $N_2O$ pulse chemisorption.

9. A process for producing an extruded shaped catalyst body according to claim 1, comprising the:
(a) combining (i) at least one aqueous solution of copper compounds, aluminum compounds, manganese compounds, and optionally transition metal compounds and (ii) at least one aqueous carbonate-containing solution to form a precipitate, isolating the precipitate, optionally washing the isolated precipitate, and drying the isolated precipitate to give a dried precipitate,
(b) forming a mixture of the dry precipitate obtained in (a) with an aluminum-containing binder selected from the group consisting of boehmite and pseudoboehmite, the aluminum-containing binder being peptized by treatment with acid,
(c) extruding the mixture obtained in step (b), to give an extrudate, and
(d) calcining the extrudate obtained in step (c), at a temperature in the range from 300 to 750° C. to give a calcined extrudate.

10. The process as claimed in claim 9, wherein step (b) comprises:
(b1) calcining dried precipitate obtained in step (a) at a temperature in the range from 250° C. to 900° C. to give a calcined precipitate,
(b2) mixing dried precipitate obtained in step (a) with calcined precipitate obtained in step (b1) in a weight ratio of dried precipitate to calcined precipitate in the range from 2:98 to 98:2, to give a mixture, and
(b3) forming a mixture of the mixture obtained in step (b2) with an aluminum-containing binder selected from the group consisting of boehmite and pseudoboehmite, the aluminum-containing binder being peptized by treatment with acid.

11. The process as claimed in claim 9, wherein the aluminum-containing binder is peptized by addition of an acid before the aluminum-containing binder is mixed with the dry precipitate.

12. The process as claimed in claim 9, wherein the acid is selected from the group consisting of acetic acid and citric acid.

13. The process as claimed in claim 9, wherein the binder has a pore volume in the range of 300-700 mm$^3$/g the pore volume being determined by mercury intrusion to DIN 66133.

14. A shaped catalyst body according to claim 1, wherein providing the copper, manganese and aluminum-containing dried precipitate
comprises combining (i) at least one aqueous solution of copper compounds, aluminum compounds, manganese compounds, and optionally transition metal compounds and (ii) at least one aqueous carbonate-containing solution to form a precipitate, isolating the precipitate, optionally washing the isolated precipitate, and drying the isolated precipitate to give a dried precipitate.

15. The shaped catalyst body according to claim 1, wherein Cu is present in an amount in the range of 24-42 wt %, Al is present in an amount in the range of 25-34 wt %, and Mn is present in the range of 2-8 wt %.

16. The shaped catalyst body according to claim 1, wherein the Cu is essentially in the form of copper oxide, copper-aluminum spinel, copper-manganese spinel, or any mixture of two or more thereof; the Al is essentially in the form of aluminum oxide, copper-aluminum spinel, or a mixture thereof, and the Mn is essentially in the form of manganese oxide, copper-magnesium spinel, or a mixture thereof.

17. A shaped catalyst body, comprising Cu in an amount in the range of 24-42 wt %, Al in an amount in the range of 25-34 wt %, and Mn in an amount in the range of 2-8 wt %, based on the total weight of the shaped catalyst body,
wherein the shaped catalyst body has a pore volume in the range from 250 to 700 mm$^3$/g, determined by mercury intrusion to DIN 66133, and
wherein the shaped catalyst body has a monomodal pore radius distribution and wherein 50% or more of the pore volume is formed by pores having a pore radius in the range from 7 to 40 nm, the pore radius distribution and the pore volume being determined by mercury intrusion to DIN 66133, and
wherein the shaped catalyst body is in the form of a calcined extrudate and has a side crushing strength, based on the length of the extrudates, in the range from 5 to 40 N/mm, the side crushing strength being determined to DIN EN 1094-5.

18. A shaped catalyst body according to claim 17, wherein the shaped catalyst body has a diameter in the range from 1 to 6 mm.

19. A shaped catalyst body in extruded form, comprising Cu in an amount in the range of 20-43 wt %, Al in an amount in the range of 20-40 wt %, and Mn in an amount in the range of 1-10 wt %, based on the total weight of the shaped catalyst body in extruded form,
wherein the shaped catalyst body has a pore volume in the range from 250 to 700 mm$^3$/g, determined by mercury intrusion to DIN 66133, and
wherein the shaped catalyst body is in the form of a calcined extrudate and has a side crushing strength, based on the length of the extrudates, in the range from 5 to 40 N/mm, the side crushing strength being determined to DIN EN 1094-5, and
wherein the shaped catalyst body has a monomodal pore radius distribution and wherein 50% or more of the pore volume is formed by pores having a pore radius in the range from 7 to 40 nm, the pore radius distribution and the pore volume being determined by mercury intrusion to DIN 66133, and
wherein the shaped catalyst body is obtained by a process comprising:
(a) combining (i) at least one aqueous solution of copper compounds, aluminum compounds, manganese compounds, and optionally transition metal compounds and (ii) at least one aqueous carbonate-containing solution to form a precipitate, isolating the precipitate, optionally washing the isolated precipitate, and drying the isolated precipitate to give a dried precipitate,
(b1) calcining dried precipitate obtained in step (a) at a temperature in the range from 250° C. to 900° C. to give a calcined precipitate,
(b2) mixing dried, uncalcined precipitate obtained in step (a) with calcined precipitate obtained in step (b1) in a weight ratio of dried precipitate to calcined precipitate in the range from 2:98 to 98:2, to give a mixture, and
(b3) forming a mixture of the mixture obtained in step (b2) with an aluminum-containing binder selected from the group consisting of boehmite and pseudoboehmite, the aluminum-containing binder being peptized by treatment with acid,
(c) extruding the mixture obtained in step (b), to give an extrudate, and (d) calcining the extrudate obtained in step (c), at a temperature in the range from 300 to 750° C. to give the calcined extrudate.

* * * * *